United States Patent
Khalili

Patent Number: 6,013,080
Date of Patent: *Jan. 11, 2000

[54] TAMP WITH HORIZONTAL STEPS USED FOR IMPACTION BONE GRAFTING IN REVISION FEMUR

[75] Inventor: Farid Bruce Khalili, Chestnut Hill, Mass.

[73] Assignee: Johnson & Johnson Professional, Inc., Raynham, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/961,044

[22] Filed: Oct. 30, 1997

[51] Int. Cl.$^7$ ........................................... A61F 5/00
[52] U.S. Cl. .................... 606/86; 606/93; 623/23
[58] Field of Search .................. 606/85, 84, 81, 606/79, 86, 94, 93, 92; 623/23

[56] References Cited

U.S. PATENT DOCUMENTS

| | | |
|---|---|---|
| 4,068,324 | 1/1978 | Townley et al. . |
| 4,552,136 | 11/1985 | Kenna ........................................ 606/85 |
| 4,704,686 | 11/1987 | Aldinger . |
| 4,800,875 | 1/1989 | Ray . |
| 4,846,839 | 7/1989 | Noiles . |
| 4,921,493 | 5/1990 | Webb, Jr. et al. ........................ 606/85 |
| 5,047,035 | 9/1991 | Mikhail et al. . |
| 5,108,405 | 4/1992 | Mikhail et al. . |
| 5,129,904 | 7/1992 | Illi . |
| 5,192,283 | 3/1993 | Ling et al. . |
| 5,454,815 | 10/1995 | Geisser et al. ............................. 606/85 |
| 5,456,686 | 10/1995 | Klapper et al. . |
| 5,470,336 | 11/1995 | Ling et al. . |
| 5,601,564 | 2/1997 | Gustilo et al. . |
| 5,681,315 | 10/1997 | Szabo ........................................ 606/85 |
| 5,704,940 | 1/1998 | Garosi ........................................ 606/85 |
| 5,766,261 | 6/1998 | Neal et al. ............................... 623/16 |

*Primary Examiner*—Michael Buiz
*Assistant Examiner*—Julian W. Woo
*Attorney, Agent, or Firm*—Nutter, McClennen & Fish, LLP

[57] ABSTRACT

A tamp system includes a plurality of tamps, each of which includes an elongated body having a stepped outer surface. The body has a diameter and a longitudinal axis, wherein the diameter decreases from a proximal end to a distal end thereof. The stepped outer surface includes a plurality of steps each having a distal-facing surface and a side-facing surface. Each tamp is adapted for compacting morsellized bone matter in a canal in a bone. The compacted bone matter can be used to resize the canal for a new prosthesis in a prosthesis revision surgery.

15 Claims, 5 Drawing Sheets

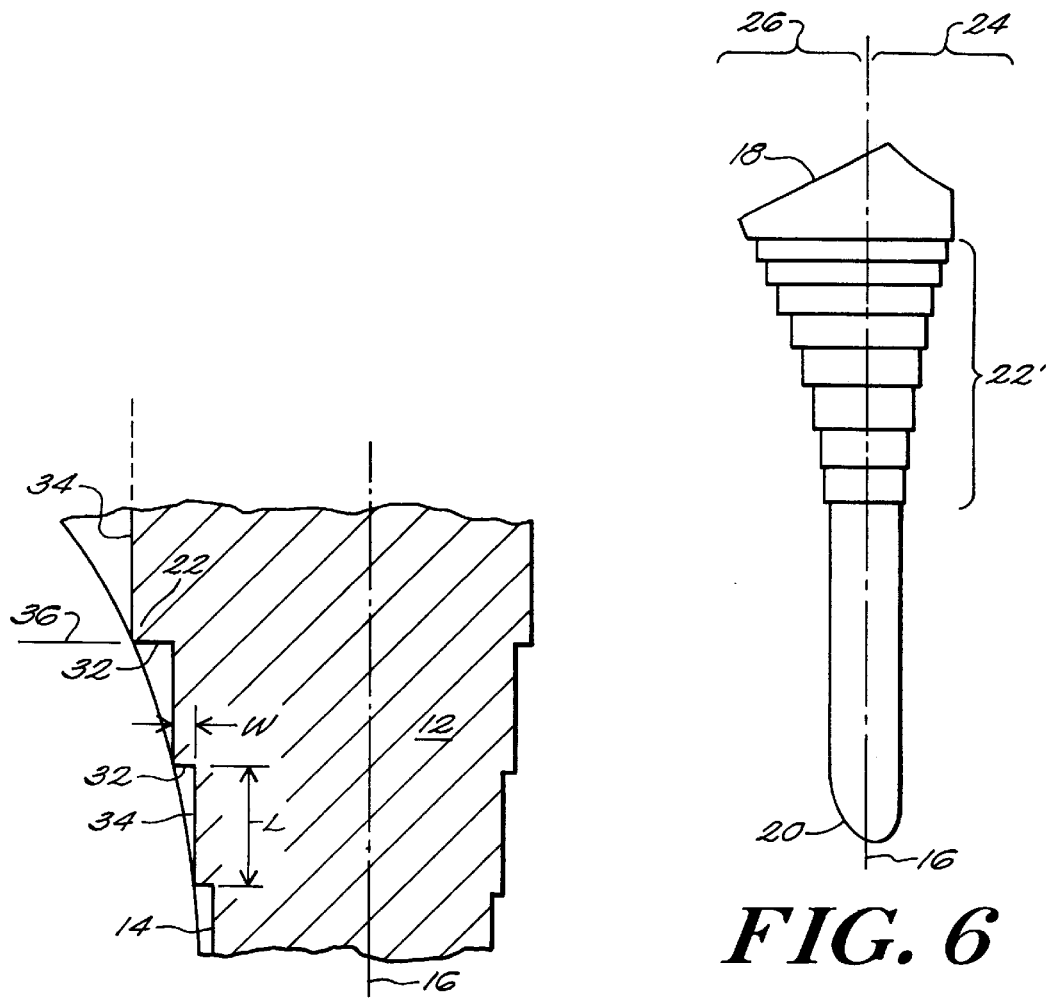
FIG. 7
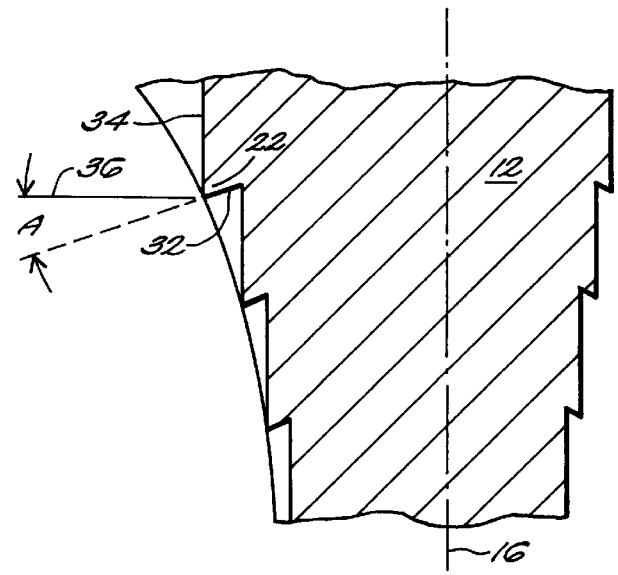
FIG. 6
FIG. 8

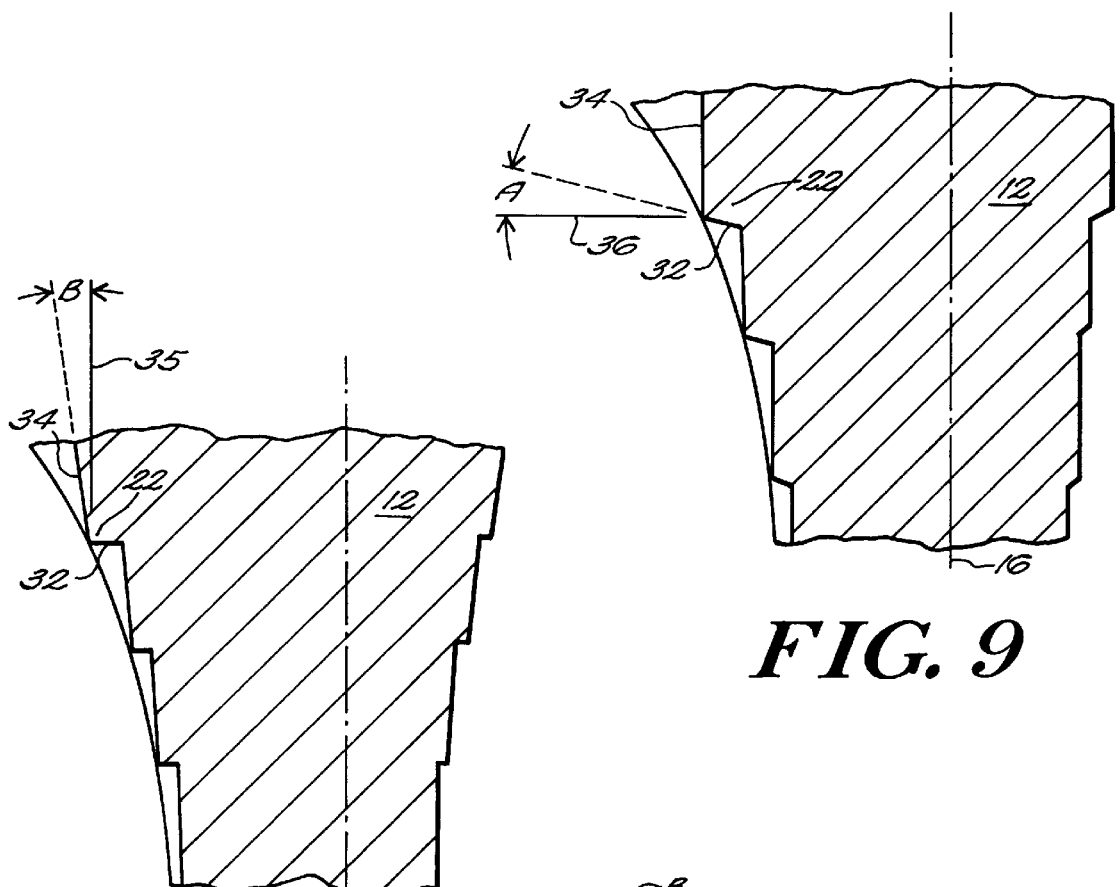
FIG. 9
FIG. 10
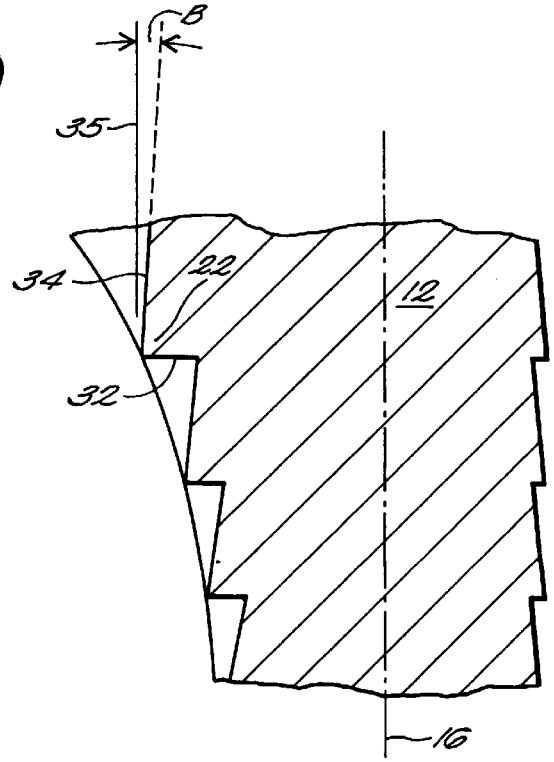
FIG. 11

TAMP WITH HORIZONTAL STEPS USED FOR IMPACTION BONE GRAFTING IN REVISION FEMUR

CROSS REFERENCE TO RELATED APPLICATION

Not Applicable.

STATEMENT REGARDING FEDERALLY SPONSORED RESEARCH

Not Applicable.

BACKGROUND OF THE INVENTION

Prosthetic implants can be used to replace natural joints that have been damaged or have deteriorated. For example, hip joint replacement surgery includes implanting a prosthetic femoral component into a prepared cavity in the femur of a patient. The femoral component is secured within the femur by an interference fit and bone ingrowth, by bone cement, or by a combination of these techniques.

Revision surgery, or replacement of a previously implanted prosthesis, may be required in some cases, usually due to long-term wear and/or subsidence of the implant.

In a revision procedure, the implanted prosthetic component is first removed from the medullary canal of the femur. Any bone cement used to secure the removed implant, and any cement-retaining plugs, must also be extracted, typically by drilling and reaming. After removal of the bone cement and plug, much of the cancellous bone is removed and usually only cortical bone remains. The resulting cavity will normally be larger than is desired to accommodate a new prosthesis, and the cortical bone will not allow cement inter-digitation to an extent sufficient to support the new prosthesis.

To reduce the size of this cavity or canal in the bone, morsellized cancellous bone from a donor can be placed in the femoral canal. This bone matter is compacted against the cortical bone with a tamp. FIG. 1 shows a typical prior art tamp 5 having a smooth outer surface that matches the contour of the prosthesis to be implanted. See also, U.S. Pat. No. 5,470,336, which is incorporated by reference herein. Alternating steps of adding bone matter and compacting the bone matter with tamps of decreasing size can be used to size the canal to generally conform to the shape of the implant.

During such a process, the cancellous bone should be sufficiently compacted to remain intact as the new implant and/or bone cement are inserted into the canal. Since the surface of the compacted bone matter interfaces with the bone cement, and/or the prosthetic implant, the compacted bone must be able to withstand shear forces that occur at the interface with the bone matter. If the cancellous bone is not adequately compacted, the strength of the interface surface can be compromised resulting in an unsuccessful revision.

While implant-shaped tamps can provide sufficient radial compaction of the morsellized bone, only limited axial compaction is achieved. The absence of adequate compaction in a longitudinal (axial) direction can leave the compacted bone matter vulnerable to damage from shear forces that result following implant revision surgery.

SUMMARY OF THE INVENTION

The present invention provides a tamp, and a system of tamps, that is useful in compacting a material in a cavity. More particularly, the tamp is useful for compacting morsellized bone matter in a cavity formed in a bone as a result of a surgical procedure such as hip replacement revision surgery. The tamp compacts the morsellized bone matter in both radial and axial directions within the cavity to recreate a cavity of sufficient size and strength to accept a replacement hip prosthesis. Although the tamp is primarily described and illustrated in conjunction with compacting bone matter in a prepared cavity formed in a femur, it is understood that the tamp can be used in other applications as well.

In one embodiment, the tamp device of the invention includes an elongate body having an outer surface with a cross-section that decreases from proximal to distal end of the elongate body. A plurality of steps are formed on the outer surface wherein each of the steps extends around the circumference of the elongate body and each step has a distal-facing surface and a side-facing surface. The stepped outer surface of the tamp is effective to compact bone matter in both radial and axial directions to form a reconstructed bone cavity of sufficient strength to withstand shear forces that develop following revision surgery.

The tamp is well-suited for implant revision surgery where a morsellized bone matter is used to prepare a bone graft to recreate a cavity in a bone that is of sufficient size and shape to receive a revision prosthesis. Morsellized bone matter is placed in the canal and it is compacted against walls of the canal with the tamp. Alternating steps of inserting additional bone matter and compacting the material with increasingly smaller tamps shape the canal to generally conform to the new implant. The stepped outer surfaces of the tamps compact each layer of morsellized bone in axial and radial directions.

BRIEF DESCRIPTION OF THE DRAWINGS

The invention will be more fully understood from the following detailed description taken in conjunction with the accompanying drawings, in which:

FIG. 6 is a front view of an alternative embodiment of the tamp of FIG. 2;

FIG. 7 is a cross sectional view of a portion of the tamp of FIG. 4 along lines 7—7;

FIG. 8 is a cross sectional view of an alternative embodiment of the tamp of FIG. 7;

FIG. 9 is a cross sectional view of another alternative embodiment of the tamp of FIG. 7;

FIG. 10 is a cross sectional view of a further alternative embodiment of the tamp of FIG. 7;

FIG. 11 is a cross sectional view of a still further alternative embodiment of the tamp of FIG. 7;

DETAILED DESCRIPTION OF THE INVENTION

Figure 1:
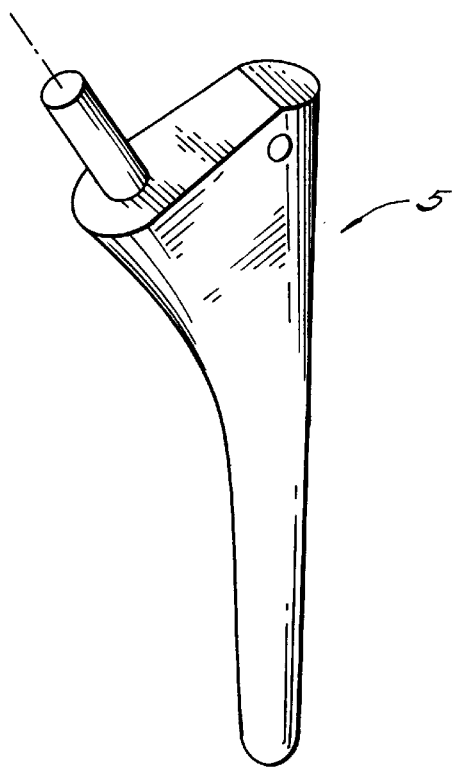
FIG. 1 is a perspective view of a prior art tamp.
Figure 2:
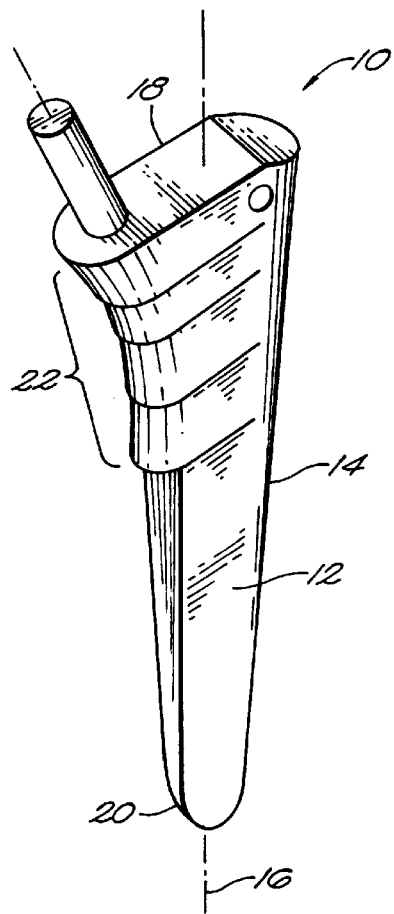
FIG. 2 is a perspective view of a tamp in accordance with the present invention.

The drawings are understood to be illustrative of the concepts disclosed herein to facilitate comprehension of the invention. Further, the drawings are not to scale, and the scope of the invention is not to be limited to the particular embodiments shown and described herein.

The invention provides a tamp, and a tamp system, in which each tamp has a stepped outer surface that offers enhanced axial compaction of a material within a bone cavity. It is understood that axial compaction, as described herein, refers to compaction in a direction substantially parallel to a longitudinal axis of the cavity. The invention is particularly applicable to compacting morsellized bone matter in a cavity formed in a bone, and especially during implant revision surgery where the cavity may need to be resized and grafted with cancellous bone to accept the new implant. Although the present invention is described in conjunction with impaction bone grafting in a femur, it is understood that the invention can be adapted for use with a variety of bones, materials and components.

Referring to FIGS. 2–5, a tamp 10 includes an elongate body 12 having a longitudinal axis 16 and an outer surface 14 with a circumference or diameter that decreases from the proximal end 18 to the distal end 20 of the elongate body. A plurality of steps 22 are formed on the outer surface 14 of the elongate body to facilitate compaction of morsellized bone matter placed in a cavity formed in a bone, as described below.

Figures 3, 4, 5:
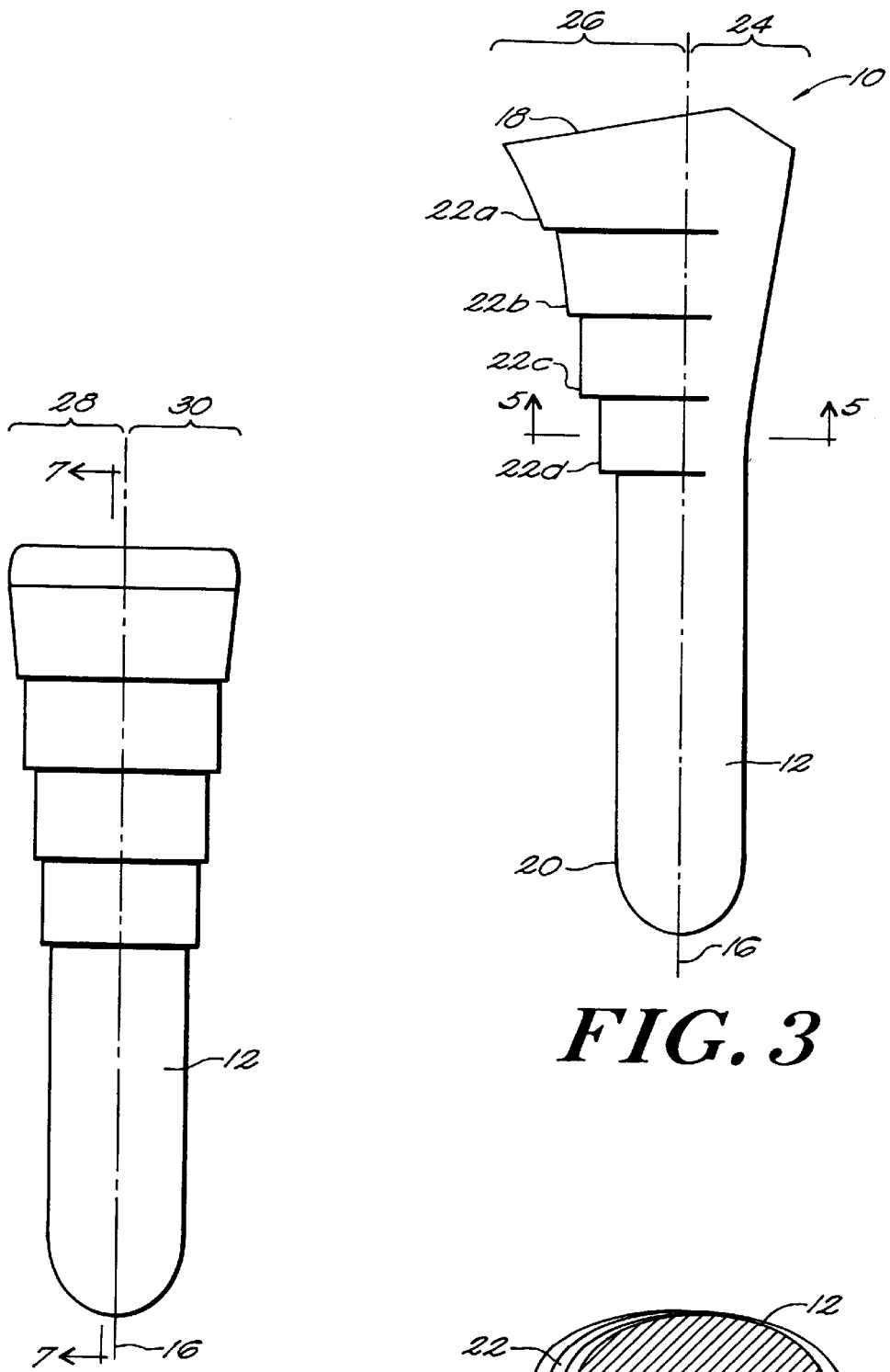
FIG. 3 is a front view of the tamp of FIG. 2.
FIG. 4 is a side view of the tamp of FIG. 2.
FIG. 5 is a cross sectional view of the tamp of FIG. 3 along lines 5—5.

As shown in FIG. 3, the longitudinal axis 16 divides the elongate body 12 into a lateral portion 24 and a medial portion 26. As shown in FIG. 4, the longitudinal axis 16 divides the body 12 into an anterior portion 28 and a posterior portion 30.

The geometry of the steps 22 can vary in relation to the overall size of the tamp, the size of the prosthesis, the amount of bone matter to be compacted, and the particular bone to be prepared to receive an implant. It is understood that each step can be of equal size, proportional in size, or unique in size with respect to other steps. The steps can be continuous, or can be formed of discrete portions disposed about the circumference of the tamp. It is further understood that the steps can vary in one or more dimensions as the steps extend circumferentially about the outer surface of the tamp. The steps can also vary in size in longitudinal and/or radial directions. Although shown as being relatively flat, it is understood that the step surfaces can be arcuate, including being convex and concave in shape. The steps can undulate along the circumference of the body, or they can be generally planar. Also, the length of the elongate body over which the steps are formed can vary. Other such modifications and alterations will be apparent to one of ordinary skill in the art and are understood to be within the scope of the invention.

In an exemplary embodiment shown in FIGS. 2–5, each of the steps 22 extend about the anterior, medial, and posterior portions 28,26,30 of the circumference of the elongate body 12. At least a part of the lateral portion 24 is generally smooth along a length of the elongate body 12. The steps 22 are most pronounced along the medial portion 26 of the elongate body 12 during the maximum rate of change in diameter of the elongate body. That is, the steps 22 extend the greatest distance from the elongate body 12 where the elongate body tapers most dramatically along the medial surface.

In an alternative embodiment shown in FIG. 6, the steps 22' extend about the entire circumference of the elongate body including the lateral portion 24.

As shown in FIG. 7, each of the steps 22 has a distal-facing surface 32 and a side-facing surface 34. The distal-facing surface 32 and the side-facing surface 34 can form a range of angles in relation to the longitudinal axis 16 and to each other.

In the exemplary embodiment of FIG. 7, the distal-facing surface 32 is generally perpendicular to the longitudinal axis 16 and the side-facing surface 34 is substantially parallel to the longitudinal axis. Thus, the distal-facing surface 32 and the side-facing surface 34 form an angle of about ninety degrees with respect to each other.

FIGS. 8–11 show alternative embodiments of the steps 22, and in particular the step surfaces 32,34. In FIGS. 8 and 9, the distal-facing surface 32 of the step forms an angle A with respect to a line 36 normal to the longitudinal axis 16 of the elongate body 12. The angle A can be in the range of about 0 degrees to about 20 degrees. Further, angle A may be canted proximally (FIG. 9) or distally (FIG. 8).

In FIG. 10 and 11, the side-facing surface 34 forms an angle B with respect to a line 35 drawn parallel to the longitudinal axis 16. The angle B can range from about 0 to about 20 degrees, and may be canted laterally (FIG. 10) or medially (FIG. 11) in relation to the longitudinal axis 16. It is understood that the angles A and B can vary about the circumference of the tamp.

The overall size of the distal-facing and side-facing surfaces 32,34, can vary depending on the desired pitch for the steps, the size of the tamp, and the taper of the tamp circumference. The width (W) (FIG. 7) of the distal-facing surface 32 can range from about 0.25 to about 6.00 millimeters and the length (L) (FIG. 7) of the side-facing surface 34 can range from about 2.00 to about 10.00 millimeters. In a preferred embodiment, the width (W) of the distal-facing surface 32 is about 2.00 millimeters and the length (L) of the side-facing surface 34 is about 7.00 millimeters.

The number of steps 22 formed on the outer surface 14 of the tamp can vary depending on the size of the steps, the size of the tamp, the desired step pitch and the intended application. The number of steps 22 can vary from about one to about fifty, and more preferably from about three to about six. In an exemplary embodiment, the tamp has about five steps.

The spacing of the steps 22 can range from about 0.5 millimeter apart to about 5.0 millimeters apart, and more preferably, from about 1.0 millimeter to about 2.0 millimeters apart. The spacing is measured from intersections of respective distal-facing and side-facing surfaces.

The overall length and outer circumference of the tamp 10 can vary depending on the anatomical requirements of a patient, the dimensions of a prosthetic component to be implanted, and the condition of a canal in a bone subsequent to removal of a prior prosthesis.

The overall length of the tamp can vary from about three to about ten inches, and preferably from about four to five inches. The overall cross-sectional area of the tamp varies along the length of the elongate body. It is understood that the cross-section of the tamp can vary to accommodate relatively large bone canals and relatively small bone canals. One of ordinary skill in the art can readily determine a tamp of appropriate size for a given canal.

A bone compaction system can include a number of proportionally sized tamps to sequentially compact layers of morsellized bone. The number of tamps comprising the system can range from about two tamps to about twenty tamps and preferably about three to four tamps. It is understood that a tamp can be selected to provide a desired thickness for the compacted bone layer and to size the canal to receive a given prosthesis.

The tamp 10 can include an extension member (not shown) that extends from the proximal end 18 of the tamp to serve as a handle. The extension member can include an impact surface at its proximal end to facilitate impaction of the tamp into the canal. A surgeon or other medical personnel can strike the impact surface with a surgical mallet or other such device to compact the morsellized bone matter.

Figure 12:
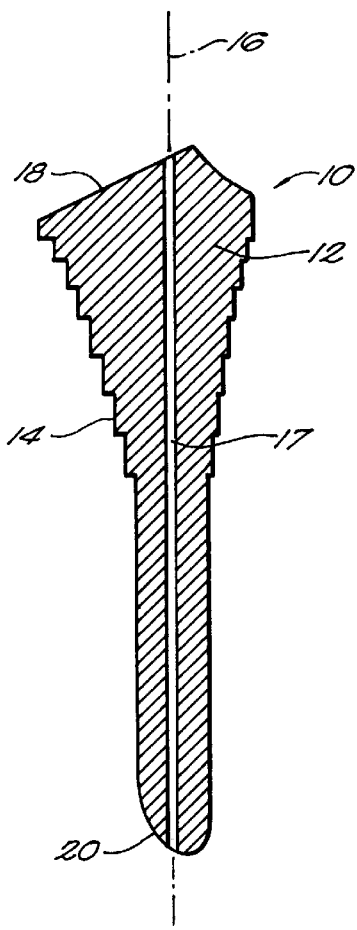
FIG. 12 is a cross sectional view of another embodiment of the tamp of FIG. 4 along lines 7—7.

In FIG. 12 the tamp is cannulated along the longitudinal axis 16 to include a passageway 17 extending from the proximal end 18 to the distal end 20. Movement of the tamp may be guided by a wire in the passageway 17 during insertion of the tamp in the canal.

As noted above, the tamp of the present invention is well suited for use in preparing a bone for implant revision surgery. As a prosthesis wears or subsides in the bone cement, the prosthesis must be removed and replaced with a new prosthesis through a revision procedure. After removal of the original prosthesis, any bone cement used to secure the original prosthesis and cement plug must be extracted from the cavity within the femur.

After the original implant and the cement are removed, the resulting cavity may be larger than is desired for implantation of an appropriate size replacement prosthesis. Further, the amount of remaining cancellous bone may be insufficient for interdigitation with bone cement.

Figure 13:
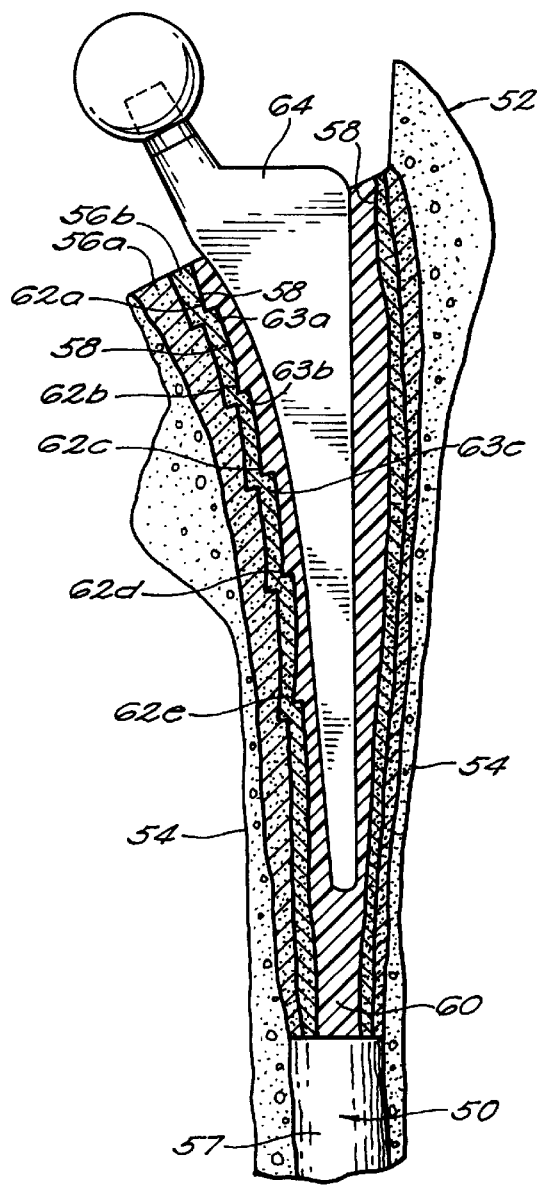
FIG. 13 is a cross sectional view of prosthesis implanted within a canal in a bone prepared with the tamp of FIG. 2.

FIG. 13 shows a cavity 50 in a femur 52 prepared with a tamp system in accordance with the present invention. The cavity 50 is formed by cortical bone 54 which remains after removal of the original prosthesis. To size the cavity 50 to dimensions appropriate for the revision prosthesis, morsellized bone matter 56a is inserted into the cavity 50. A plug 57 can be inserted at a distal end of the cavity 50 to retain the bone matter. A tamp of a suitable size is inserted into the cavity 50 to compact the bone matter 56a against the cortical bone 54. Additional morsellized bone can be placed in the cavity 50 and a smaller tamp can then be used to compact the bone matter to form a further layer 56b of compacted bone. Thus, the compacted bone matter 56 can be formed in layers to accommodate a given revision prosthesis.

The stepped outer surface 14 of the tamp 10 causes the morsellized bone matter to be compacted in both radial and axial directions. As the tamp 10 is inserted in the cavity 50, the steps 22, and in particular the distal-facing surfaces 32, compact the bone matter 56 in a direction along the longitudinal axis 16 of the tamp. Radial compaction of the bone matter is achieved as axial force is applied to the tamp during insertion into the cavity 50. The side-facing surfaces 34 force bone matter radially outward against the cortical bone 54.

Generally, the cavity is sized to be slightly larger than the contour of the new prosthesis to provide a gap between a surface 58 of the compacted bone 56 and the prosthesis. The gap can be filled with bone cement 60 to secure the prosthesis in the bone cavity 50.

The surface 58 of the compacted bone is a mirror image of the outer surface 14 of the tamp 10. Thus, the surface 58 includes a series of steps 62 with corresponding outermost portions 63 at a crest of the steps. As an implant 64 is inserted into the canal 50, the outermost portions 63 of the steps 62 are compressed against the previous layer of compressed cancellous bone chips. The stepped surface 58 of the bone matter is effective to minimize shear loads between the surface 58 of the compacted bone matter and the cement 60. Thus, shear forces between layers of compacted cancellous bone 56 are reduced and the outermost portions 63 of the cancellous bone layer 56 are compressed against the cortical bone 54.

The tamp system of the present invention can be formed from a variety of materials having high strength and durability. Examples of such materials include metal alloys such as cobalt chromium alloys, stainless steel, ceramics and other materials that are well known for use in the manufacture of tamps. A preferred material for the tamp is stainless steel.

One skilled in that art will realize further features and advantages of the invention from the above-described embodiments. Accordingly, the invention is not to be limited by what has been particularly shown and described, except as indicated by the appended claims. All publications and references cited herein are expressly incorporated herein by reference in their entirety.

What is claimed is:

1. A tamp device for compacting a material in a cavity, comprising:

an elongate body having proximal and distal ends, an outer surface and a longitudinal axis, the outer surface having a cross-section that decreases from the proximal end to the distal end thereof; and a plurality of steps formed in the outer surface wherein each of the steps has a distal-facing surface and a side-facing surface, and each side-facing surface has a length that extends from a proximal end of the side-facing surface to a distal end of the side-facing surface, wherein adjacent distal-facing surfaces and side-facing surfaces intersect to form respective compacting crests, and the distal-facing surfaces of the steps are proximally canted to form an angle of less than about twenty degrees with a normal to the longitudinal axis of the body;

wherein each of the distal-facing surfaces of the plurality of steps extends further from the longitudinal axis than an adjacent, distally located distal-facing surface, such that each distal-facing surface is effective to longitudinally compact the material as the tamp is inserted into the cavity.

2. The device according to claim 1 wherein the side-facing surface is parallel to the longitudinal axis.

3. The device according to claim 1 wherein the side-facing surface is tapered from the proximal end of the side-facing surface to the distal end of the side-facing surface.

4. The device according to claim 1, wherein the material includes morsellized bone.

5. The device according to claim 1, wherein the cavity is in a bone and is adapted to receive a prosthetic component.

6. The device according to claim 1, wherein the elongate body has approximately three to six steps formed therein.

7. The device according to claim 6, wherein the length of each step, extending from proximal end to the distal end thereof, is in the range of about two to about ten millimeters.

8. The device according to claim 1, wherein each step extends about a circumference of the elongate body.

9. The device according to claim 1, wherein the elongate body is cannulated along the longitudinal axis.

10. A system for compacting a morsellized bone material in a bone cavity, comprising:

a plurality of tamps of differing sizes, each of the plurality of tamps including an elongate body with a proximal end and a distal end, the elongate body having an outer surface, and a longitudinal axis; and a plurality of compacting steps formed in the outer surface wherein each of the steps extends about the outer surface of the elongate body and has a distal-facing surface and a side-facing surface, each side-facing surface having a length that extends from a proximal end of the side-facing surface to a distal end of the side-facing surface, the distal-facing surfaces of the steps being proximally canted and forming an angle of less than about twenty degrees with a normal to the longitudinal axis of the body, wherein each of the distal-facing surfaces of the plurality of steps extends further from the longitudinal axis than an adjacent, distally located distal-facing surface, such that each distal-facing surface longitudinally compacts the material as the tamp is inserted into the cavity.

11. The system according to claim 10, wherein the outer surface of each tamp has a cross-sectional area that decreases from the proximal end to the distal end thereof.

12. The system according to claim 10, wherein the side-facing surface of each step of one of the tamps is substantially parallel to the longitudinal axis of the tamp.

13. The system according to claim 10, wherein the side-facing surface of each step of one of the tamps is tapered from a proximal end of the side-facing surface to a distal end of the side-facing surface.

14. The system according to claim 10, wherein each tamp has approximately two to about ten steps formed therein.

15. The system according to claim 14, wherein the length of each step, extending from the proximal end of the side-facing surface to the distal end of the side-facing surface, is in the range of about two to about ten millimeters.

* * * * *